(12) United States Patent
Pedersen et al.

(10) Patent No.: US 6,329,182 B1
(45) Date of Patent: Dec. 11, 2001

(54) METHOD OF PRODUCING OLIGOSACCHARIDE SYRUPS, A SYSTEM FOR PRODUCING THE SAME AND OLIGOSACCHARIDE SYRUPS

(75) Inventors: Sven Pedersen, Gentofte; Hanne Vang Hendriksen, Holte, both of (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/200,109

(22) Filed: Nov. 25, 1998

(30) Foreign Application Priority Data

Nov. 26, 1997 (DK) ................................................ 1356/97

(51) Int. Cl.[7] ................................................. C12P 19/20
(52) U.S. Cl. ................................ 435/96; 435/95; 435/99; 435/100; 210/651; 210/652; 210/654; 127/55
(58) Field of Search ........................... 435/96, 95, 99, 435/100; 210/651, 652, 654; 127/55

(56) References Cited

U.S. PATENT DOCUMENTS

| | | | |
|---|---|---|---|
| 4,254,225 | * | 3/1981 | Tamura et al. .......................... 435/96 |
| 4,511,654 | * | 4/1985 | Rohrbach et al. ....................... 435/95 |
| 5,130,237 | * | 7/1992 | Thomas et al. ......................... 435/96 |
| 5,869,297 | * | 2/1999 | Binder et al.. ......................... 435/105 |

FOREIGN PATENT DOCUMENTS 0 301 522 A2   2/1989 (EP) .
0 452238 A  *  10/1991 (EP) .

OTHER PUBLICATIONS

Handbook of Amylases and Related Enzymes, Their Sources, Isolation Methods Properties and Applications, The Amylase Research Society of Japan, pp. –214–217, (1988).

A. Harder et al., Kinetics of Isomaltose Formation By Amyloglucosidase and Purification of theDisaccharide by Fermentation of Undesired By–Products, (1983).

* cited by examiner

*Primary Examiner*—Francisco Prats
(74) *Attorney, Agent, or Firm*—Elias J L Ambiris; Jason I Garbell (57) ABSTRACT

The present invention relates to a method of producing oligosaccharide syrups, in particular to the production of syrups having a high concentration of saccharides with a degree of polymerization of at least 2, comprising the steps of: enzymatic reaction of a substrate at a temperature in the range of 50° C. to 100° C. obtaining a saccharide solution comprising monosaccharides and disaccharides, trisaccharides and higher saccharides; nanofiltration of the saccharide solution at a temperature in the range of 60° C. to 100° C. obtaining a syrup essentially comprising disaccharides, trisaccharides and higher saccharides; recovering said syrup; optionally recycling the permeate resulting from the nanofiltration step to the enzymatic reaction.

20 Claims, 3 Drawing Sheets

Nanofiltration
Oligosaccharide production

Alternative set-up without the RO unit for water removal

METHOD OF PRODUCING OLIGOSACCHARIDE SYRUPS, A SYSTEM FOR PRODUCING THE SAME AND OLIGOSACCHARIDE SYRUPS

CROSS-REFERENCE TO RELATED APPLICATIONS

This application claims priority under 35 U.S.C. 119 of Danish application 1356/97 filed Nov. 26, 1997, the contents of which are fully incorporated herein by reference.

TECHNICAL FIELD

The present invention relates to a method of producing oligosaccharide syrups, in particular to the production of syrups having a high concentration of saccharides with a degree of polymerization of at least 2.

Oligo- and disaccharide mixtures are used industrially, in particular in the food industry, such as in bakeries, confectioneries, soft drinks and saké production.

Oligosaccharide syrups with a low concentration of monosaccharides are advantageous in the field of low caloric additives in many food applications, such as sweeteners, dietary fibers or bulking agents, where they are employed in ice-cream and dairy products, chocolate preparations, chewing gum, biscuits, fruit preparations, pharmaceutical preparations and animal fodder. Due to the low content of monosaccharides the syrups do not cause caries or other dental diseases.

Furthermore, oligosaccharides find use in the drug industry, where for example interest is growing for saccharide adhesion molecules, such as bacterial or leucocyte adhesion.

Oligo- and disaccharide syrups may be produced by enzymatic conversion of starch into sugars followed by enzymatic reactions of the sugars. Enzymatic conversion of starch into sugars involves the steps of liquefaction and saccharification. By the subsequent enzymatic reactions it is possible to obtain a content of disaccharides of 10% to 30%, and of particular disaccharides, such as isomaltose, of 10% to 28% by weight calculated on the basis of dry substance (DS) of syrup.

Handbook of Amylases and Related Enzymes, Ed. by The Amylase Research Society of Japan, Pergamon Press, pp 215–217 discloses a process of producing oligosaccharide mixtures, wherein the content of monosaccharides is 40.5%, disaccharides is 28.3%, trisaccharides is 19.0%, the rest being higher saccharides.

Harder et al. (Kinetics of Isomaltose Formation by Amyloglucosidase and Purification of the Disaccharide by Fermentation of Undesired By-Products, Annals New York Academy of Sciences, Biochemical Engineering 3, vol. 413, pp. 340–351, 1983) suggested to increase the yield of isomaltose in a syrup, in laboratory scale, by fermentation of some of the by-products from the enzymatic reaction of glucose to isomaltose, i.e. glucose and maltose, by *Saccharomyces cerevisiae* and subsequent extraction of glycerol formed by the fermentation. The process involved several steps to achieve an isomaltose content of about 96.5% by weight on the basis of dry substance. This process, however, does not apply in an industrial scale.

Until now it has not been possible to obtain a syrup enriched in disaccharides and/or higher saccharides in industrial process lines.

It is an object of the present invention to provide a method of producing an oligosaccharide syrup comprising the steps of:

enzymatic reaction of a substrate at a temperature in the range of 50° C. to 100° C. obtaining a saccharide solution comprising monosaccharides and disaccharides, trisaccharides and higher saccharides, nanofiltration of the saccharide solution at a temperature in the range of 60° C. to 100° C. obtaining a syrup essentially comprising disaccharides, trisaccharides and higher saccharides, recovering said syrup, optionally recycling the permeate resulting from the nanofiltration step to the enzymatic reaction, whereby it is possible to obtain an oligosaccharide syrup having a high content of saccharides of a degree of polymerisation of at least 2.

The permeate comprising monosaccharides may be used as substrate for the enzymatic reaction saving a considerable amount of substrate and reducing the total costs involved in the method. In a continuous method, this can be achieved by recycling the permeate material to the enzyme reactor directly by having a direct passage to the enzyme reactor from the nanofiltration unit. Alternative, the permeate may be stored for later use.

It is another object of the present invention to provide a system for producing oligosaccharide syrups comprising an enzyme reactor having at least one inlet and at least one outlet and means for controlling the temperature in the tank, means for passing saccharide solution from the reactor outlet(s) to at least one nanofiltration unit, at least one nanofiltration unit having a nanofiltration membrane dividing the nanofiltration unit into an entrance side having at least one inlet and at least one outlet, and an exit side having at least one outlet, and having means for controlling the pressure applied to the membrane, optionally means for recycling material from an outlet of the exit side of the nanofiltration unit to the enzyme reactor.

It is yet another object of the present invention to provide a disaccharide syrup obtainable by the method, wherein the ratio by weight of disaccharide to total dry substance is from at least 40%, preferably at least 50%, most preferably at least 70%, and the ratio by weight of monosaccharide to total dry substance is from 0.5% to 30%, preferably 0.5% to 20%, most preferably 0.5% to 10% the balance being trisaccharides and higher saccharides.

A further object of the present invention is an oligosaccharide syrup obtainable by the method, wherein the ratio by weight of monosaccharide to total dry substance is at most 10%, preferably at most 5% and the ratio by weight of saccharides having a polymerization degree from 2 to 6 to total dry substance is at least 90%.

Another object of the present invention is a method for using the permeate from the method, for example as a method of producing at least 55% pure fructose, comprising the steps of:

enzymatic reaction of glucose and fructose at a temperature in the range of 50° C. to 80° C. obtaining a saccharide solution comprising glucose and fructose, and disaccharides, trisaccharides and higher saccharides, nanofiltration of the saccharide solution at a temperature in the range of 60° C. to 80° C. obtaining a syrup essentially comprising disaccharides, trisaccharides and higher saccharides, recovering said syrup, and recovering the permeate resulting from the nanofiltration step.

In the present context all percentages are calculated as percent by weight on basis of dry substance (DS) unless otherwise indicated.

In the present context "oligosaccharide syrup" means a syrup comprising monosaccharides (DP1), disaccharides (DP2), trisaccharides (DP3) and higher saccharides (DP4+). By the term a disaccharide syrup is meant that the major part of the saccharides are disaccharides.

The notation DP1, DP2, DPX refers to the degree of polymerization of the saccharide, i.e., DP1 is a polymerization degree of 1 (monosaccharide), DP 2 is a disaccharide, and DPX is a polymerization degree of X.

BRIEF DESCRIPTION OF THE DRAWINGS

The present invention is further illustrated by reference to the accompanying drawings wherein.

DETAILED DISCLOSURE OF THE INVENTION

Enzymatic Reaction Step

The enzymatic reaction is typically carried out in one stage in an enzyme reactor wherein the enzymes are contacted with the substrate for the enzymatic reaction.

Typically, the substrate is constituted by one type of monosaccharide only, for example glucose, fructose, galactose, UDP-galactose, mannose, or xylose. However, in some embodiments the substrate may be a mixture of at least two different monosaccharides, such as glucose and fructose. The choice of substrate is of course depending on the composition of the oligosaccharide syrup to be produced. The monosaccharide substrate may be passed to the enzyme reactor in essentially pure form, such as 95% monosaccharide on dry substance.

In one embodiment of the invention the substrate for the enzymatic reaction is liquefied starch solution or maltodextrins whereby the enzymatic reaction is carried out as a combination of a saccharification reaction followed by the enzymatic reaction leading to disaccharides, trisaccharides and higher saccharides. By combining the saccharification and the enzymatic reaction it is possible to save several steps in the process. The combined reactions are preferably carried out in at least two stages in the enzyme reactor, more preferably more stages.

By saccharification, maltodextrins (liquefied starch solution) are subjected to the action of an enzyme, typically hydrolysed, to convert the starch solution into monosaccharides.

In another embodiment of the invention, disaccharides, such as sucrose and lactose, are used as the substrate.

The enzymatic reaction is carried out at a temperature in the range of 50° C. to 100° C., typically the temperature is in the range from 60° C. to 100° C., such as from 63° C. to 80° C., preferably from 65° C. to 75° C. It has been shown that this temperature interval secures a high yield of the saccharides to be produced, while at the same time secures a microbially stable environment in the enzyme reactor.

The enzymatic reaction is conducted at a pH appropriate for the selected enzyme. pH is preferably from 4 to 5.5.

In one aspect of the present invention diasaccharide syrups are produced. When producing disaccharide syrups the enzymatic reaction is typically a reverse hydrolysis reaction.

Any appropriate hydrolysing enzymes may be used for the reverse hydrolysis, in particular those selected from the group consisting of glucoamylase, α-glucosidase, β-glucosidase (cellobiase), β-galactosidase, α-galactosidase, xylobiase, β-mannosidase, α-mannosidase, and arabinofuranosidase.

Examples of reverse hydrolysis reactions:

A particular preferred enzymatic reaction is the production of isomaltose syrup from a substrate comprising a mixture of glucose and fructose, such as a mixture wherein fructose is from 40% to 50% and glucose is from 46% to 56%, preferably fructose is from 42% to 46% and glucose is from 50% to 54%. By this reaction enriched isomaltose syrup is obtained. Furthermore, the permeate obtained comprising at least 55% fructose also constitutes a product employable in various fields.

The enzymatic reaction is a reverse hydrolysis carried out at a temperature interval from 50° C. to 80° C. and a pH suitable for the enzyme.

The isomaltose syrup is obtained as described below.

The permeate obtained comprises at least 55% fructose and can be evaporated or subjected to reverse osmosis to increase the content of dry matter before use.

In another aspect of the present invention transferase enzymes are employed in the enzymatic reaction. Examples of appropriate enzymes are fructosyltransferase, dextransucrase, transglucosidase, sialyltransferase, and fucosyltransferase.

Examples of reactions of transferases:

Another enzymatic reaction may be a kinase reaction, such as a glucosylkinase reaction.

Preferably, the enzymatic reaction of the invention is performed in the presence of a heatstable or thermostable enzyme to improve the yields and reduce costs. By the terms heatstable and thermostable are meant that the enzyme is stable at the selected temperature for a sufficient period to carry out the enzymatic reaction. Often a heatstable enzyme has increased stability compared to wild type enzyme at 60° C.

In a preferred embodiment of the present invention heatstable glucoamylase enzymes are utilised for the enzymatic reaction. The glucoamylase enzyme may preferably be derived from a strain of Aspergillus, in particular *Aspergillus niger*, a strain of Clostridium, in particular *Clostridium thermoamylolyticum*, *Clostridium thermosulphurogenes*, *Clostridium thermohydrosulphuricum*, a strain of Pestalotiopsis, or a strain of Talaromyces, in particular *Talaromyces duponti*, *Talaromyces emersonii* and *Talaromyces thermophilus*.

In the embodiments of the invention wherein the enzymatic reaction comprises saccharification of liquefied starch solution the saccharification step may be performed in presence of a thermostable de-branching enzyme. Preferably, the de-branching enzyme is a pullunase (EC 3.2.1.41) or an isoamylase (EC 3.2.1.68). The thermostable pullunase may be derived from a strain of Bacillus, in particular *Bacillus naganoenis*, a strain of Clostridium, in particular *Clostridium thermosulphurogenes* and *Clostridium thermohydrosulphuricum*, or a strain of Pyrococcus, in particular *Pyrococcus woesie* and *Pyrococcus furiosus*.

The thermostable isoamylase may be derived from a strain of Flavobacterium, in particular *Flavobacterium odoratum*.

In a further embodiment, the saccharification step may be performed in presence of a thermostable α-amylase, preferably a fungal α-amylase. A fungal α-amylase may be derived from a strain of Aspergillus, in particular *Aspergillus niger*, or a strain of Acremonium.

The enzymatic reaction may be conducted with soluble enzymes in a membrane reactor whereby the enzymes are separated from the saccharide solution produced and retained in the enzyme reactor.

In a preferred embodiment of the invention the enzymatic reaction is conducted with immobilised enzymes, e.g., in a column reactor. Immobilised enzymes are exemplified by microcapsules in which enzymes are entrapped in a particle with a semipermeable polyamide membrane. The substrates and the products of the enzymatic reaction may diffuse through the membrane.

By predetermined setting of the following parameters for the enzymatic reaction:

Temperature

Reaction time

Enzyme dosage

Substrate concentration

Substrate mixture

Substrate ratio of one type to another it is possible to determine the amounts and ratios of monosaccharide, disaccharide, trisaccharide and higher saccharides in the saccharide solution.

The temperature setting is depending on the enzyme selected. By a specific temperature setting the reaction time may be controlled by taking samples from the enzyme reactor periodically to monitor the enzymatic reaction.

The ratios of the various saccharides in the saccharide solution have been shown to be of great importance for the result of the nanofiltration.

It has been found that to produce a highly enriched disaccharide syrup the amount of trisaccharide and higher saccharides should be as low as possible in the saccharide solution. To obtain this it has been shown that it is necessary to keep the concentration of the disaccharide in the saccharide solution low as well. The level for the disaccharide concentration depends on the specific reaction, and in particular on the reaction equilibrium. The concentration should preferably be below 40% on DS.

In case of isomaltose the concentration of disaccharides should be from 5% to 30%, more preferably from 10% to 20% in the saccharide solution.

Nanofiltration Step

In the context of the present invention nanofiltration means a membrane separation having a cut-off value of a molecular weight of 300–1,000, for comparison see table 1 with respect to other filtration processes. Monovalent ions can pass fairly freely through a nanofiltration membrane together with water. Polyvalent negative ions are rejected almost completely by a good nanofiltration membrane.

TABLE 1

Typical Membrane Cut-off Values

| Type of Membrane Separation | Cut-off Values (Molecular Weight) |
|---|---|
| Microfiltration | 100,000 to 1,000,000 |
| Ultrafiltration | 2,000 to 100,000 |
| Nanofiltration | 300 to 1,000 |
| Reverse Osmosis | Less than 100 |

EP 0 452 238 disclose a process for nanofiltering a food processing stream which begins with a starch slurry and ends with a glucose syrup which is 95% dextrose and 5% di- and trisaccharides. After the nanofiltration the material may be considerably more than 99% pure dextrose. The nanofiltration is preferably carried out in a temperature range from 120° F. to 145° F. EP 0 452 238 describes a process of concentrating a monosaccharide (dextrose) in the permeate from the filtration step, and is silent with respect to a process for concentrating higher saccharides than monosaccharides.

The present inventors have found that by conducting nanofiltration in a temperature range of 60° C. to 100° C. it is possible to obtain an oligosaccharide syrup with a low content of undesired monosaccharides. In a preferred embodiment the nanofiltration is operated at a temperature in the range of 63° C. to 90° C., such as from 65° C. to 80° C.

In a preferred embodiment of the invention the nanofiltration step is conducted at essentially the same temperature as the enzyme reaction step thereby obviating the need for heating or cooling the saccharide solution before it enters the nanofiltration step.

Any nanofiltration membrane which is functional at the selected temperature may be used in the present invention. An example of a good nanofiltration membrane is the Desal 5 series, commercially available from Osmonics Desal.

A preferable nanofiltration membrane should have the following characteristics:

When operated at 70° C., 20–30 atm and a flux of 12–33 kg/(m²h) filtrating a syrup of the following composition:

| | |
|---|---|
| Syrup DS: | 38 to 42% |
| Syrup composition: | DP1–61% |
| | DP2–26% |
| | DP3+–13% |
| | (approximate values ± 4%) | the membrane should preferably retain at least 90% DP2 and at most 30% DP1.

The feed stream for the nanofiltration membrane is constituted of the saccharide solution produced in the enzymatic reaction step. The feed stream is passed by the nanofiltration membrane under a sufficient pressure to separate the monosaccharides from the higher saccharides. Preferably, the pressure is above 10 atm, such as 10 to 30 atm.

In one embodiment of the invention the feed stream is pumped to the nanofiltration membrane whereby the pump creates the pressure differential through the membrane. A reduction valve then controls the pressure.

The nanofiltration step is operated so as to secure an appropriate content of dry matter at the membrane. In case the content of dry matter rises to a critical value the filtration process will diminish reducing the effeciency of the filtration or even stop. Accordingly, it is of importance to monitor the content of dry matter at the membrane and optionally add water to the feed stream. In one embodiment of the invention the nanofiltration step comprises diafiltration whereby water is added to the feed stream. Preferably, the water added corresponds to the amount of permeate.

By using diafiltration a larger amount of the monosaccharides present in the feed stream may be filtered, thus increasing the content of saccharides of a polymerisation degree $\geq 2$ on basis of the total dry substance in the syrup.

In a preferred embodiment the content of saccharides of a polymerisation degree $\geq 2$ on basis of the total dry substance in the syrup is at least 80%, such as 90%.

The syrup is recovered from the nanofiltration unit. The syrup may be evaporated or subjected to reverse osmosis to increase the content of dry substance by eliminating water.

In one embodiment of the invention a disaccharide syrup is produced. In such a syrup the ratio of disaccharide to total dry substance in the syrup is at least 40%, preferably at least 50%, more preferably at least 70% and the ratio by weight of monosaccharide to total dry substance is from 0.5% to 30%, preferably 0.5% to 20%, most preferably 0.5% to 10%, the balance being trisaccharides and higher saccharides.

In a preferred embodiment of the invention the composition of the disaccharide syrup is as follows:

|  | % $DP_x$ on dry substance |
| --- | --- |
| monosaccharides (DP1) | 0.5–30% |
| disaccharides (DP2) | 50–99% |
| trisaccharides (DP3) | 0.01–20% |
| higher saccharides (DP4+) | 0.01–10% |

In another preferred embodiment of the invention an isomaltose syrup is produced. In the isomaltose syrup isomaltose constitutes about 80% of the disaccharide present. Preferably the isomaltose syrup comprises at least 40% isomaltose, such as at least 50% isomaltose, most preferably at least 70% isomaltose, the balance being monosaccharides, other disaccharides, trisaccharides and higher saccharides.

In another embodiment of the invention an oligosaccharide syrup is produced wherein substantially all the saccharides have a polymerization degree of 2 to at least 10, preferably 2 to 6, such as at least 80% of the saccharides, more preferably 90% of the saccharides. In a preferred embodiment the monosaccharide content is at most 10% in the oligosaccharide syrup.

For oligosaccharide syrups for use as low caloric additives it is preferred that as little sucrose as possible is present. Therefore, the enzymatic reaction typically includes hydrolysing the sucrose to monosaccharides before entering the nanofiltration unit.

Permeate

In a preferred embodiment of the invention the permeate is recycled to the enzyme reactor for the monosaccharides present in the permeate to be used as substrate for the enzymatic reaction.

When entering the enzyme reactor the recycled permeate should preferably have the same dry substance concentration as the substrate led to the enzyme reactor from other sources.

In another embodiment of the invention the permeate is not recycled to the enzyme reactor but used for other purposes. This is especially interesting when the permeate comprises large amounts of fructose, such as at least 55% fructose, see above.

When leaving the nanofiltration unit the ratio by weight of monosaccharides to total dry substance in the permeate is preferably at least 80%, more preferably at least 90%.

To adjust the overall content of dry substance, essentially monosaccharides only, in the permeate excess water may be removed by reverse osmosis before the permeate enters the enzyme reactor.

The method of producing oligosaccharide syrups may be conducted as a continuous method, in which substrate is continuously fed to the enzyme reactor, optionally combined with continuously recycled permeate. By a continuous method there is no need for storage or cooling of the saccharide solution thereby reducing the risk of bacterial contamination, and furthermore, the costs involved in the production are reduced.

In another embodiment of the invention the method is conducted as a batch method, in two separate processes, an enzymatic reaction process and a nanofiltration process. In a batch method, it is possible to optimize the nanofiltration step independent of the enzymatic reaction, thereby achieving a more efficient nanofiltration.

Furthermore in a preferred embodiment of the present invention, a combination of a continuous and a batch process may be envisaged, in that at least two nanofiltration units are coupled to the enzyme reactor, whereby one nanofiltration unit is used at a time. When this unit has been filled, the saccharide solution from the enzymatic reaction will be directed to the other unit(s). After the filling of the nanofiltration unit the nanofiltration step is then conducted as a batch process. By this combination the advantages from both methods are achieved.

System

Figure 1:
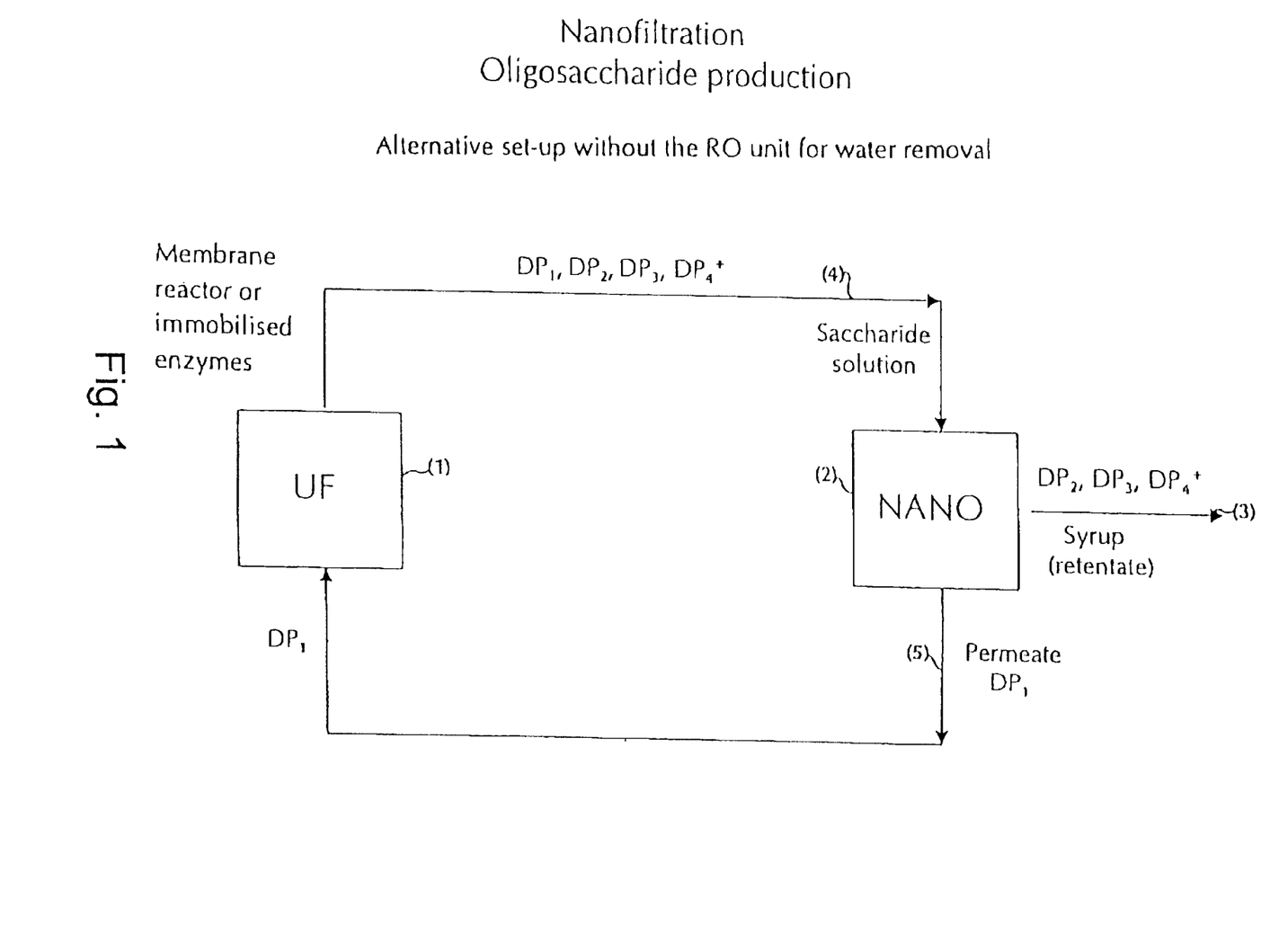
FIG. 1 is a schematic presentation of the system according to invention.
Figure 2:
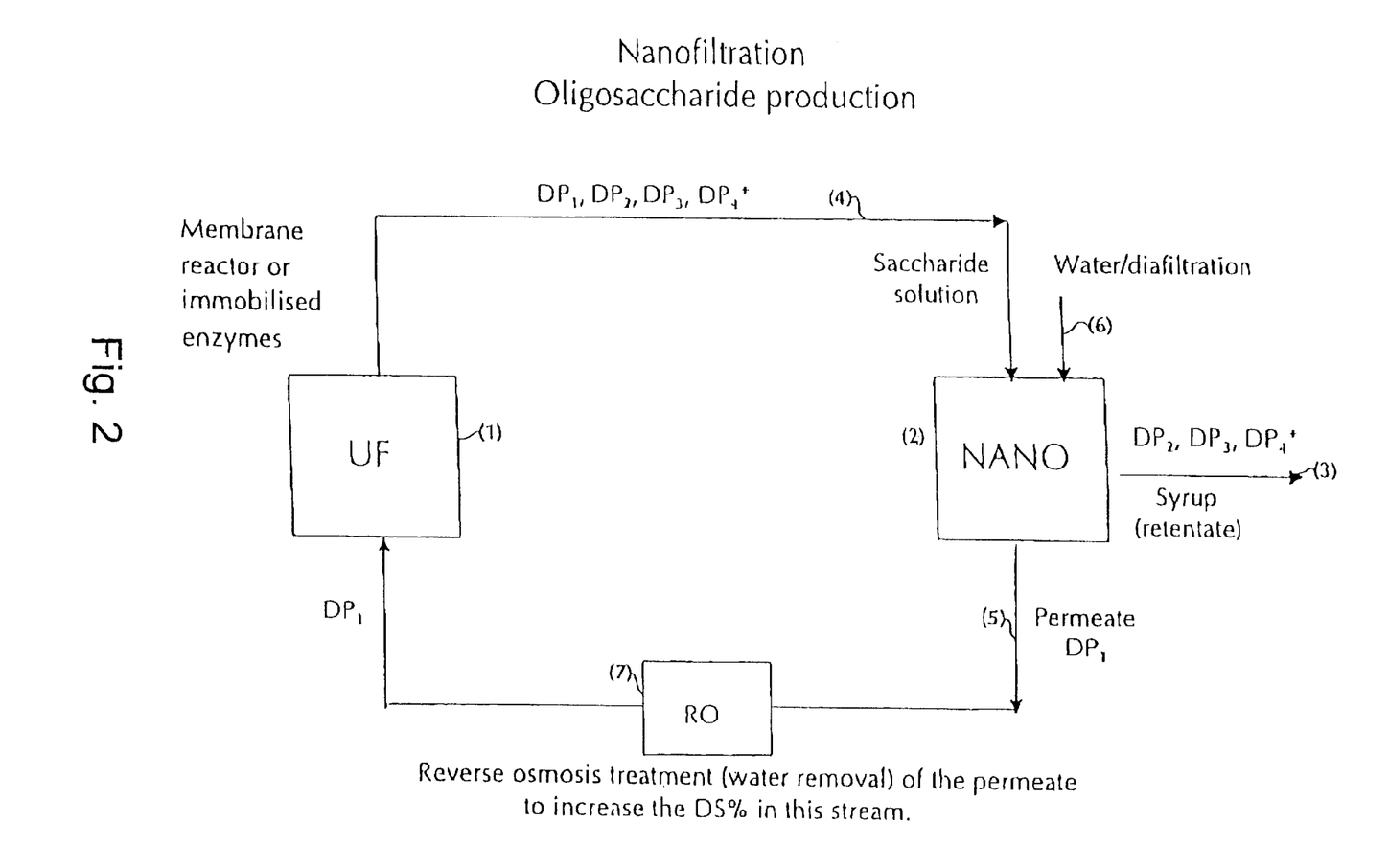
FIG. 2 is a schematic presentation as of FIG. 1, wherein the system is operated as a diafiltration and additionally comprises means for reverse osmosis of the permeate recycling to the enzyme reactor.
Figure 3:
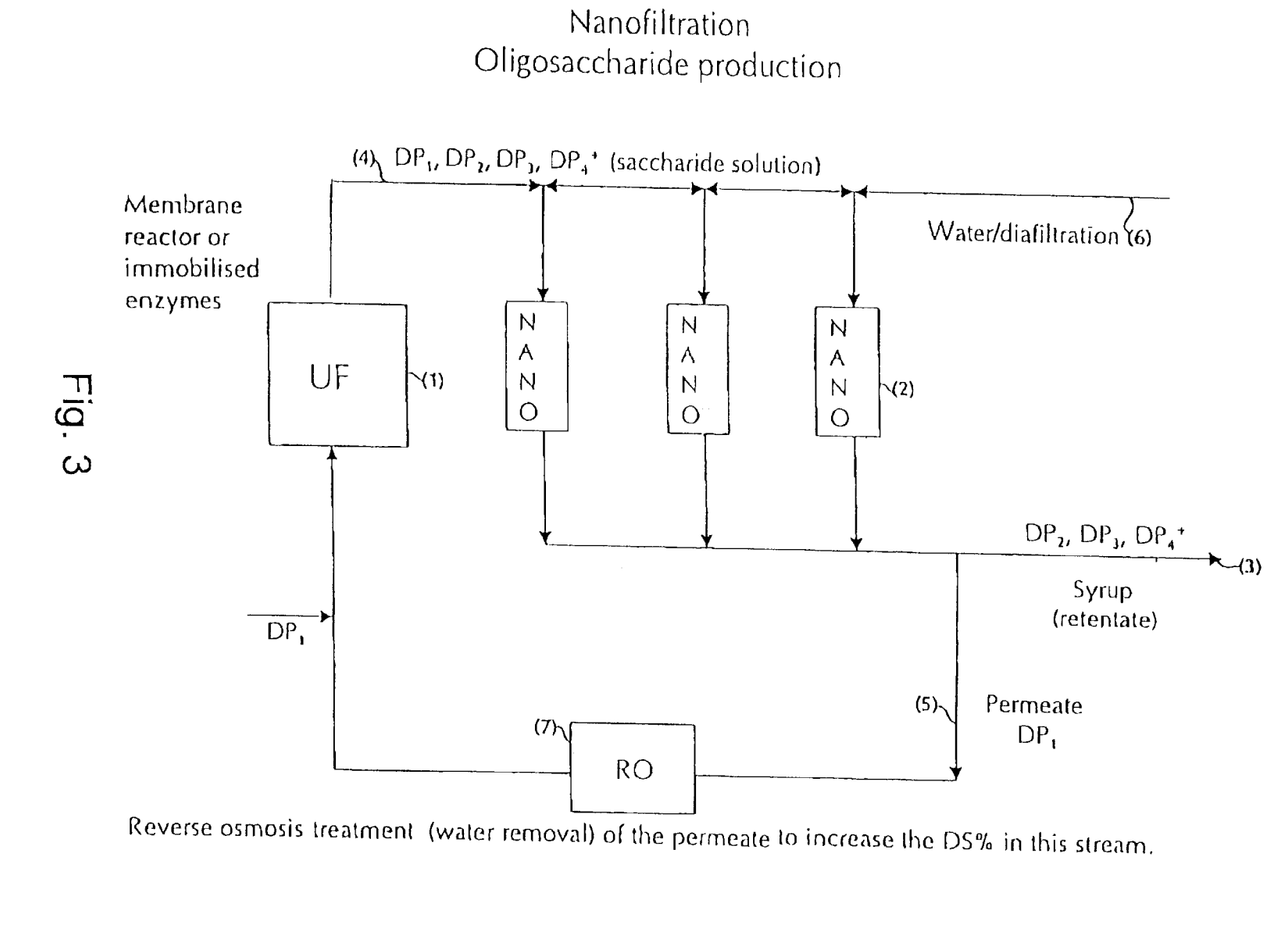
FIG. 3 is a presentation of another embodiment of the system according to the invention wherein the enzyme reactor is connected to three nanofiltration units arranged in parallel.

The invention further comprises a system for producing an oligosaccharide syrup comprising an enzyme reactor 1 having at least one inlet and at least one outlet and means for controlling the temperature in the tank, means 4 for passing saccharide solution from the reactor outlet(s) to at least one nanofiltration unit 2, at least one nanofiltration unit 2 having a nanofiltration membrane dividing the nanofiltration unit into an entrance side having at least one inlet and at least one outlet 3, and an exit side having at least one outlet 5, and having means for controlling the pressure applied to the membrane, optionally means for recycling material from an outlet 5 of the exit side of the nanofiltration unit 2 to the enzyme reactor 1.

In one embodiment the enzyme reactor 1 further comprises means for taking samples of the saccharide solution during the enzymatic reaction in order to monitor the reaction.

In a batch mode or a combined continuous/batch mode the enzyme reactor 1 may be operated with at least two nanofiltration units 2, each unit being filled and operated at a time. However, operating the system as batch mode is of course also possible with one nanofiltration unit 2 only.

The enzyme reactor 1 is typically a membrane reactor, however, in a preferred embodiment it is a column reactor. The column rector may be packed with enzymes entrapped in membranes, as described above.

By utilizing a column reactor it is possible to create several stages of enzymatic reaction by packing different enzymes in various sections of the reactor or by varying the concentration of enzymes entrapped in the membranes.

The nanofiltration unit 2 is typically driven with a pump and a pressure release valve or a reduction valve. The pump is driven to produce the pressure differential over the nanofiltration membrane.

The system is fed with a feed stream through the at least one inlet. When the nanofiltration unit 2 is operated as a diafiltration water may directed to the feed stream to the nanofiltration unit 2 or be added to the nanofiltration unit through another inlet 6.

The permeate leaves the nanofiltration unit 2 from the at least one outlet 5 in the exit side. In a preferred embodiment of the system means for reverse osmosis 7 is provided in the permeate stream in the outlet 5 of the nanofiltration unit 2 or downstream the outlet 5 in order to concentrate the content of dry substance in the permeate.

In another embodiment the permeate may be evaporated to increase the dry substance content.

EXAMPLES

The invention is further illustrated with reference to the following examples which are not intended to be in any way limiting the scope of the invention as claimed.

Example 1
Production of High-Isomaltose Syrup in a Batch Method
Enzyme reaction:

A 40% DS glucose solution was prepared and pH adjusted to 4.5. Enzyme, 10 AG/g DS of AMG 300 L (Novo Nordisk A/S) was added and the mixture incubated at 60° C. The reaction was run at constant pH in a pH-stat.

Samples were taken periodically and the sugar spectrum analyzed using IMPC HPLC. After incubation for 48 hours the enzyme was inactivated by heating the liquor to 90° C. for 30 minutes.

The saccharide solution was then filtered, carbon treated and stored cold. The final composition are shown in table 2.

TABLE 2

| Composition of the saccharide solution % DPx on DS | | | | |
|---|---|---|---|---|
| DP1 | maltose* | isomaltose | DP3 | DP4+ |
| 77.76 | 3.87 | 14.24 | 3.37 | 0.77 |

*The solution contains small amounts of other disaccharides (e.g. nigerose) which are co-eluted with maltose.

Membrane Filtration

The produced saccharide solution (approximately 2 kg) was membrane filtered using a Desal 5-series, DL, Durasan™ nanofiltration membrane from Osmonics Desal (membrane characteristics are given in table 3).

TABLE 3

| Membrane characteristics | |
|---|---|
| Membrane: | Thin film composite polysulfone |
| Nominal rating: | <100 molecular weight cutoff |
| MgSO$_4$ rejection: | 96% |
| Typical operating pressure: | 10–30 bar |
| Maximum pressure: | 40 bar |
| Maximum temperature: | 75° C. suggested |
| Recommended pH: | Operating range 4–11.0 |
| Cleaning range: | 2–11.5 |
| Chlorine tolerance: | 1000 ppm–hours |

The membrane system was a plate-and-frame module with a total membrane area of 720 cm$^2$. The saccharide solution was heated to 70° C. and the filtration run at this temperature and a pressure of 30 bar. The process was operated as a diafiltration by continuously adding water to the feed liquid keeping the volume constant.

The process was run until a preset amount of washing water had been added. The combined values for retentate and permeate sampled during filtration are listed in table 4 below.

TABLE 4

Sugar profile of retentate and permeate
R1/P1 after 3.4 l of water,
R2/P2 after 7 l of water
R3/P3 after 17 l of water.
Disaccharides are given both as the total sum and as maltose, isomaltose respectively.

| | % DPx on DS | | | | | | (Brix) |
|---|---|---|---|---|---|---|---|
| | DP1 | DP2 | maltose* | isomaltose | DP3 | DP4+ | % DS |
| R1 | 43.2 | 45.6 | 9.1 | 36.5 | 9.3 | 1.9 | 13.4 |
| P1 | 93.7 | 6.2 | 1.2 | 5.0 | 0.1 | 0 | 3.4 |
| R2 | 19.2 | 64.0 | 12.8 | 51.2 | 13.9 | 2.8 | 7.7 |
| P2 | 85.3 | 14.4 | 2.9 | 11.5 | 0.3 | 0 | 0.8 |
| R3 | 1.7 | 75.7 | 15.1 | 60.6 | 18.7 | 3.7 | 6.3 |
| P3 | 36.9 | 63.1 | 12.6 | 50.5 | 0 | 0 | 0.1 |

*The syrup contains small amounts of other disaccharides (e.g., nigerose) which are coeluted with maltose.

As shown in the table 4 a highly enriched isomaltose syrup is obtained both after 3.5 and 7 l of water added, 36.5% and 51.2%, respectively.

In this example, by further filtration until 17 l of washing water has been added 60.6% isomaltose syrup is obtained, however the glucose content of the permeate has diminished excessively at the end of the filtration.

Example 2
Membranefiltration at Different Temperature, Pressure, and DS
Saccharide Solution The saccharide solution used in the present experiment was a 80/20% (w/w) glucose:maltose syrup prepared by dissolving relevant amounts of glucose and maltose in water at a total DS of approximately 30% (w/w).

Membrane Filtration

The saccharide solution was membrane filtered using a Desal 5-series, DL, nanofiltration membrane from Osmonics Desal (membrane characteristics are given in table 3 in Example 1). The membrane system was a labcell plate-and-frame testmodule with a total membrane area of 37 cm$^2$. The filtration was run first varying temperature, then pressure and finally at a lower bulk DS, to illustrate the effect of changing these parameters on filtration performance.

The composition of the permeate obtained at the various operational conditions are given in the tables below. Since the filtration was run in a testmodule using a very small membrane area the retentate composition did not change significantly during operation and was only analysed sporadically.

TABLE 5

Operating conditions, obtained flux over the membrane, DS and composition of permeate and bulk samples. DS in bulk approximately 28% (w/w). parameters changed are given in bold.

| Sample | Temp. °C. | Pressure atm | Flux kg/m²/h | DS Brix | DP1 | DP2 % DPx on DS | DP3⁺ |
|---|---|---|---|---|---|---|---|
| Bulk 1 | 60 | 30 |  | 27.6 | 78.93 | 19.71 | 1.36 |
| Perm 1 | 60 | 30 | 17.01 | 15.8 | 98.40 | 1.58 | 0.02 |
| Perm 2 | 70 | 30 | 25.41 | 16.3 | 98.34 | 1.65 | 0.01 |
| Perm 3 | 75 | 30 | 29.66 | 16.6 | 98.16 | 1.82 | 0.02 |
| Bulk 2 | 70 | 25 |  | 27.9 | 78.71 | 19.95 | 1.35 |
| Perm 4 | 70 | 25 | 17.61 | 17.6 | 98.05 | 1.93 | 0.02 |
| Perm 5 | 70 | 20 | 11.85 | 19.8 | 97.59 | 2.39 | 0.02 |
| Perm 6 | 70 | 15 | 7.20 | 21.4 | 96.83 | 3.14 | 0.02 |
| Perm 7 | 70 | 10 | 3.50 | 23.1 | 94.90 | 5.06 | 0.04 |
| Bulk 3 | 70 | 5 |  | 27.7 | 78.33 | 20.31 | 1.37 |
| Bulk 4 | 70 | 30 |  | 21.42 | 78.38 | 20.25 | 1.38 |
| Perm 8 | 70 | 30 | 45.47 | 9.56 | 98.50 | 1.48 | 0.02 |

TABLE 6

Concentration of glucose (DP1) and maltose (DP2) in bulk ($C_b$) and permeate ($C_p$) calculated from the results in table 5. Retention of the compounds is calculated as ($C_b - C_p$)/$C_b$ * 100. For Permeate 1–3, Bulk value 1 was used, for Permeate 4–6, Bulk value 2, for Permeate 7, Bulk value 3, and for Permeate 8, Bulk value 4. Parameters changed are given in bold.

| Sample | Temp. °C. | Pres. bar | $C_b$ (DP1) g DPx/g * 10² | $C_p$ (DP1) | Rt. DP1 % | $C_b$(DP2) g DPx/g * 10² | $C_p$ (DP2) | Rt. DP2 % |
|---|---|---|---|---|---|---|---|---|
| Bulk 1 | 60 | 30 | 21.80 |  |  | 5.44 |  |  |
| Perm 1 | 60 | 30 |  | 15.51 | 28.9 |  | 0.25 | 95.4 |
| Perm 2 | 70 | 30 |  | 16.03 | 26.5 |  | 0.27 | 95.1 |
| Perm 3 | 75 | 30 |  | 16.33 | 25.1 |  | 0.30 | 94.4 |
| Bulk 2 | 70 | 25 | 21.94 |  |  | 5.56 |  |  |
| Perm 4 | 70 | 25 |  | 17.30 | 21.2 |  | 0.34 | 93.9 |
| Perm 5 | 70 | 20 |  | 19.32 | 11.9 |  | 0.47 | 91.5 |
| Perm 6 | 70 | 15 |  | 20.72 | 5.6 |  | 0.67 | 87.9 |
| Perm 7 | 70 | 10 |  | 21.88 | −0.9 |  | 1.17 | 79.2 |
| Bulk 3 | 70 | 5 | 21.68 |  |  | 5.62 |  |  |
| Bulk 4 | 70 | 30 | 16.79 |  |  | 4.34 |  |  |
| Perm 8 | 70 | 30 |  | 9.42 | 43.9 |  | 0.14 | 96.7 |

The results obtained in the permeate clearly illustrates the effect of changing the operating conditions of the membrane unit. Different fluxes over the membrane could be obtained resulting in a different selectvity of the membrane for the two compounds. All in all this illustrates the possibilities of varying and controlling the separation process.

Example 3
Membranefiltration of a Gentiobiose Containing Saccharide Solution
Saccharide Solution The saccharide solution was produced by incubating a 70% (w/w) glucose solution, pH 6.5, 55° C. with 30 U/g DS β-glucosidase (Novozym 188 from Novo Nordisk) for 24 hours. After incubation the enzyme was inactivated by heating the liquor to 90° C. for 30 minutes. The saccharide solution was then filtered, carbon treated and stored cold. The final saccharide composition is shown in table 7. A total yield of 39% (w/w) on DS oligosaccharides was obtained. 28% (w/w) was disachharides of which gentiobiose constituted the major part followed by isomaltose and minute amounts of trehalose. 11% (w/w) was higher saccharides (DP3 and DP4).

TABLE 7

| w/w % on DS | | |
|---|---|---|
| DP1 | DP2 | DP3⁺ |
| 61 | 28 | 11 |

Membrane Filtration

The saccharide solution was membrane filtered using a Desal 5-series, DL, nanofiltration membrane from Osmonics Desal (membrane characteristics are given in table 3 in Example 1). The membrane system was a plate-and-frame module with a total membrane area of 720 cm².

The saccharide solution was diluted to approximately 25% (w/w) DS and the membranefiltration run at 70° C. and a pressure of 30 bar. The process was operated as a diafiltration by continuously adding water to the feed liquid keeping the volume constant. Whenever 500 g of permeate had left the unit the flux was calculated and samples from the bulk and permeate were taken. The samples were analysed at HPLC for determination of the sugar profile and DS was measured. Results obtained are shown in table 8.

TABLE 8

Diafiltration of a gentiobiose containing saccharide solution. Data given are flux, DS and composition of the permeate and bulk samples. The concentration of DP1 ($C_{dp1}$) and DP2 ($C_{dp2}$) in bulk and permeate were calculated as well as the retention of the compounds, i.e., Rt = ($C_b$ − $C_p$)/$C_b$ * 100 from connected values of $C_b$ and $C_p$. Only the results of every second sample are given corresponding to roughly 1000 g of permeate having left the unit for each set of samples. Filtration was run at 70° C., 30 bar. Initial DS in bulk approximately 22% (w/w).

| Sample | Flux kg/m²/h | DS Brix | DP1 | DP2 % DPx on DS | DP3+ | C (DP1) | C (DP2) g DPx/g * 10² | Rt. DP1 | Rt. DP2 % |
|---|---|---|---|---|---|---|---|---|---|
| Perm 1  | 31 | 6.68  | 98.36 | 1.61  | 0.04  | 6.57  | 011  | — | — |
| Perm 3  | 46 | 4.24  | 98.23 | 1.76  | 0.02  | 4.16  | 0.07 | — | — |
| Perm 5  | 56 | 3.22  | 97.87 | 2.13  | 0     | 3.15  | 0.07 | — | — |
| Perm 7  | 65 | 2.38  | 97.48 | 2.52  | 0     | 2.32  | 0.06 | — | — |
| Perm 9  | 71 | 1.90  | 96.97 | 3.03  | 0     | 1.84  | 0.06 | — | — |
| Perm 11 | 74 | 1.52  | 96.78 | 3.22  | 0     | 1.47  | 0.05 | — | — |
| Perm 13 | 81 | 1.22  | 96.14 | 3.86  | 0     | 1.17  | 0.05 | — | — |
| Perm 15 | 82 | 1.02  | 95.57 | 4.43  | 0     | 0.97  | 0.05 | — | — |
| Perm 17 | 88 | 0.88  | 94.79 | 5.22  | 0     | 0.83  | 0.05 | — | — |
| Bulk 1  | — | 20.60 | 57.35 | 30.46 | 12.19 | 11.81 | 6.28 | 44.4 | 98.3 |
| Bulk 3  | — | 17.96 | 51.97 | 34.41 | 13.62 | 9.33  | 6.18 | 55.4 | 98.8 |
| Bulk 5  | — | 16.50 | 47.04 | 37.94 | 15.02 | 7.76  | 6.26 | 59.4 | 98.9 |
| Bulk 7  | — | 14.92 | 42.57 | 41.14 | 16.29 | 6.35  | 6.14 | 63.5 | 99.0 |
| Bulk 9  | — | 14.02 | 38.15 | 44.18 | 17.67 | 5.35  | 6.19 | 65.6 | 99.1 |
| Bulk 11 | — | 12.94 | 35.13 | 46.41 | 18.47 | 4.55  | 6.01 | 67.6 | 99.2 |
| Bulk 13 | — | 12.08 | 31.76 | 48.70 | 19.54 | 3.84  | 5.8  | 69.4 | 99.2 |
| Bulk 15 | — | 11.50 | 28.09 | 51.13 | 20.78 | 3.23  | 5.88 | 69.8 | 99.2 |
| Bulk 17 | — | 10.66 | 24.85 | 53.14 | 22.01 | 2.65  | 5.67 | 68.5 | 99.2 |

After diafiltration of the saccharide solution (adding a total of 8.5 l water) a final syrup enriched in oligosaccharides and containing 53% (w/w) disaccharides was obtained.

Example 4
Membranefiltration of a Isomaltose/Glucose/Fructose Containing Saccharide Solution Saccharide Solution The saccharide solution is produced by incubating an approximately 80% (w/w) total DS 55/45% glucose/fructose solution, pH 4.5, 70° C. with amyloglucosidase (AMG 300 L from Novo Nordisk), 20 AGU/g glucose for 24 hours. After incubation the enzyme is inactivated by heating the liquor to 90° C. for 30 minutes. The saccharide solution is then filtered, carbon treated and stored cold. A total yield of about 20% (w/w) on DS oligosaccharides is obtained. About 12–20% (w/w) is disachharides of which isomaltose constitutes the major part followed by maltose and small amounts of nigerose.

Membrane Filtration

The saccharide solution is membrane filtered using a Desal 5-series, DL, nanofiltration membrane from Osmonics Desal (membrane characteristics are given in table 3 in Example 1). The membrane system is a plate-and-frame module with a total membrane area of 720 cm². The saccharide solution is diluted to approximately 30% (w/w) DS and the membranefiltration run at 70° C. and a pressure of 30 bar. The process is operated as a diafiltration by continuously adding water to the feed liquid keeping the volume constant. Whenever 500 g or 1000 g of permeate leave the unit the flux is calculated and samples from the bulk and permeate are taken. The samples are analysed at HPLC for determination of the sugar profile and DS is measured.

After diafiltration of the saccharide solution (adding around 10 l water) a final syrup enriched in oligosaccharides and containing about 45% (w/w) disaccharides is obtained, as well as a permeate enriched in fructose (about 55%).

What is claimed is:

1. A method for producing an oligosaccharide syrup from a glucose-containing solution comprising:
   (a) reverse hydrolysis of a glucose-containing solution with glucoamylase at a temperature in the range of 50° C. to 100° C. to form a solution comprising monosaccharides, disaccharides, trisaccharides and higher saccharides,
   (b) nanofiltration of the solution at a temperature in the range of 60° C. to 100° C. to form the oligosaccharide syrup and a permeate, and
   (c) recovering the oligosaccharide syrup, wherein the ratio of disaccharide to the total dry substance in the syrup recovered is at least 40%.

2. The method of claim 1, further comprising:
   (d) recycling the permeate to step (a).

3. The method of claim 1, wherein the reaction is conducted with immobilised glucoamylase.

4. The method of claim 3, wherein glucoamylase is entrapped in a particle with a semipermeable membrane.

5. The method of claim 1, wherein the glucoamylase is a soluble enzyme and the reaction is conducted in a membrane reactor separating the solution from the glucoamylase.

6. The method of claim 1, wherein the reaction is conducted at a temperature from 60° C. to 100° C.

7. The method of claim 1, wherein the oligosaccharide syrup is a disaccharide syrup.

8. The method of claim 7, wherein the disaccharide syrup is isomaltose syrup or gentobiose syrup.

9. The method of claim 8, wherein the isomaltose concentration in the solution is from 5% to 30%.

10. The method of claim 7, wherein the ratio of disaccharide to total dry substance in the syrup recovered is at least 50%.

11. The method of claim 10, wherein the ratio of disaccharide to total dry substance in the syrup recovered is at least 70%.

12. The method of claim 1, wherein the oligosaccharide syrup comprises a mixture of oligosaccharides having a degree of polymerization from 2 to 6.

13. The method of claim 1, wherein the nanofiltration step comprises diafiltration.

14. The method of claim 1, wherein nanofiltration is operated at a pressure of 10–30 atm.

15. The method of claim 1, wherein nanofiltration is operated at a temperature in the range of 63° C. to 90° C.

16. The method of claim 1, which is a continuous method.

17. The method of claim 1, which is conducted as a batch method.

18. The method of claim 2, wherein the recycled permeate is subjected to reverse osmosis to remove water before the permeate enters the reaction.

19. The method of claim 1, wherein the ratio by weight of monosaccharides to total dry substance in the permeate is at least 80%.

20. The method of claim 1, wherein the ratio by weight of monosaccharides to total dry substance in the permeate is at least 90%.

* * * * *